United States Patent
Kousalik et al.

(10) Patent No.: US 9,575,048 B2
(45) Date of Patent: Feb. 21, 2017

(54) METHOD FOR MONITORING AT LEAST ONE PARAMETER OF QUALITY OF YARN AND/OR PARAMETERS OF SENSOR BY ELECTRONIC YARN CLEANER

(71) Applicant: Rieter CZ s.r.o., Usti nad Orlici (CZ)

(72) Inventors: Pavel Kousalik, Usti nad Orlici (CZ); Jiri Sloupensky, Usti nad Orlici (CZ)

(73) Assignee: Rieter CZ s.r.o., Usti nad Orlici (CZ)

( * ) Notice: Subject to any disclaimer, the term of this patent is extended or adjusted under 35 U.S.C. 154(b) by 194 days.

(21) Appl. No.: 14/332,844

(22) Filed: Jul. 16, 2014

(65) Prior Publication Data
US 2015/0022814 A1    Jan. 22, 2015

(30) Foreign Application Priority Data
Jul. 16, 2013   (CZ) ...................... 2013-567

(51) Int. Cl.
*G01N 33/36*  (2006.01)
*G01B 11/24*  (2006.01)
*G01B 11/10*  (2006.01)
*G01N 21/15*  (2006.01)
(Continued)

(52) U.S. Cl.
CPC ............ *G01N 33/365* (2013.01); *D01H 13/26* (2013.01); *G01B 11/105* (2013.01); *G01B 11/2433* (2013.01); *G01N 21/15* (2013.01); *G01N 21/8915* (2013.01)

(58) Field of Classification Search
CPC ......... D01H 13/26; D01H 13/32; G01B 11/10; G01B 11/24; G01B 11/2408; G01B 11/245; G01B 11/2433; G01B 11/105;G01N 21/15; G01N 21/8915; G01N 21/8401; G01N 21/8903; G01N 21/898; G01N 21/89; G01N 2021/155; G01N 2021/157
See application file for complete search history.

(56) References Cited

U.S. PATENT DOCUMENTS 4,414,476 A * 11/1983 Maddox ............... G01B 11/26
                                                     250/235
5,221,960 A *  6/1993 Akerlind ............ B65H 63/0324
                                                     250/559.4
(Continued)

FOREIGN PATENT DOCUMENTS

EP          1 319 926 A2    6/2003
WO        WO 99/36746      7/1999

*Primary Examiner* — Gordon J Stock, Jr.
(74) *Attorney, Agent, or Firm* — Dority & Manning, P.A.

(57) ABSTRACT

A method is provided for monitoring at least one yarn quality parameter and/or a parameter of a sensor by an electronic cleaner of yarn by means of an optical detector comprising a sensor with one or two rows of individual optical elements. The individual optical elements provide at their outputs an analog signal proportional to the intensity of its irradiation, the value of which is monitored during each measurement cycle. In the first and/or the second row of optical elements of the sensor, for each monitored parameter, individual optical elements of the sensor, are selected constituting an active zone for monitoring a particular parameter. The number of the optical elements in one active zone in one row is lower than the overall number of the optical elements in the corresponding row, and the output analog signal of the individual optical elements of the corresponding active zone is included in the evaluation of the particular parameter.

12 Claims, 2 Drawing Sheets

(51) Int. Cl.
*G01N 21/89* (2006.01)
*D01H 13/26* (2006.01)

(56) References Cited

U.S. PATENT DOCUMENTS

| | | | | |
|---|---|---|---|---|
| 5,264,909 A | * | 11/1993 | Rochester | G01B 11/105 |
| | | | | 250/559.24 |
| 5,319,578 A | * | 6/1994 | Lawson | D01H 13/26 |
| | | | | 250/559.15 |
| 5,420,802 A | * | 5/1995 | Nevel | D01H 13/26 |
| | | | | 702/43 |
| 5,499,794 A | * | 3/1996 | Aeppli | G01N 21/8915 |
| | | | | 250/559.41 |
| 5,825,501 A | * | 10/1998 | Mee | G01N 21/8983 |
| | | | | 356/429 |
| 5,875,419 A | * | 2/1999 | Nevel | D01H 13/26 |
| | | | | 250/559.01 |
| 6,130,746 A | * | 10/2000 | Nevel | B65H 63/062 |
| | | | | 250/559.24 |
| 6,219,135 B1 | | 4/2001 | Hensel et al. | |
| 6,242,755 B1 | | 6/2001 | Henze et al. | |
| 6,659,386 B1 | * | 12/2003 | Rienas | B65H 63/0321 |
| | | | | 242/478.2 |
| 2015/0022813 A1 | * | 1/2015 | Kousalik | D01H 13/26 |
| | | | | 356/429 |

* cited by examiner

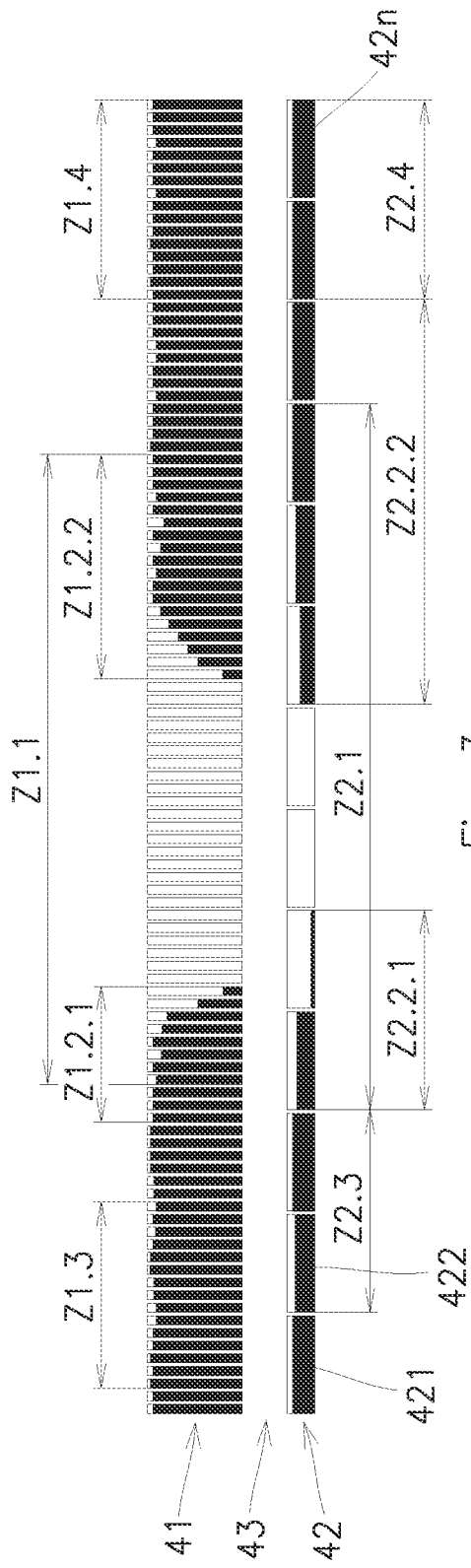
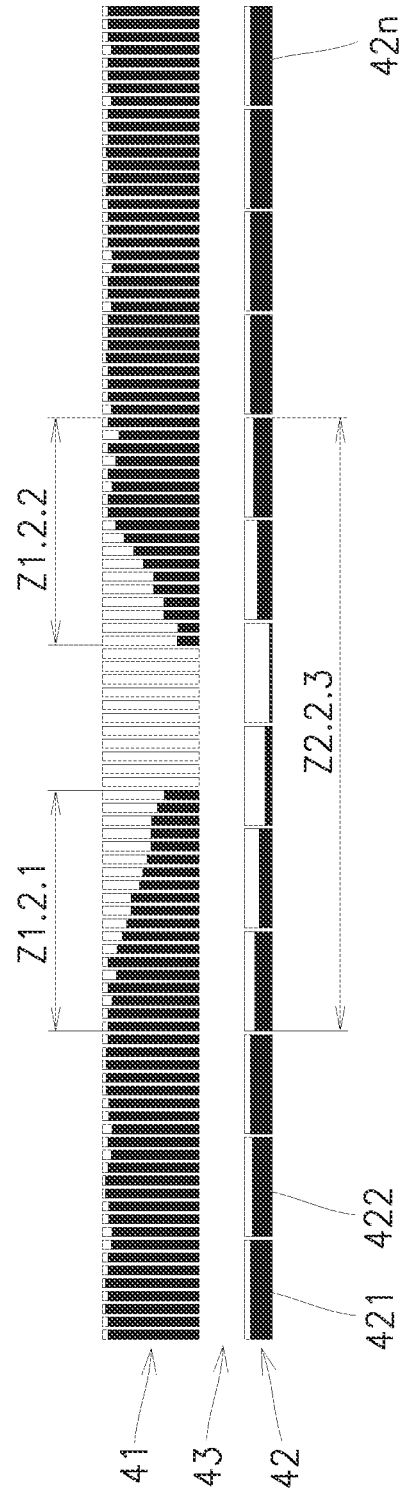
Fig. 3
Fig. 4

METHOD FOR MONITORING AT LEAST ONE PARAMETER OF QUALITY OF YARN AND/OR PARAMETERS OF SENSOR BY ELECTRONIC YARN CLEANER

TECHNICAL FIELD

The invention relates to a method for monitoring at least one yarn quality parameter and/or the parameters of a sensor by an electronic yarn cleaner by means of an optical detector having a sensor with one or two rows of individual optical elements of a rectangular shape, whereby the individual optical elements provide at their outputs an analog signal proportional to the intensity of its irradiation, the value of which is monitored during each measurement cycle.

BACKGROUND

The patent CZ 286113 (EP1051595B1) describes a method for detecting the thickness and/or homogeneity of moving yarn, in which the yarn moves in a radiation flux between a radiation source and a linear CCD detector, whereby each of the elements of the CCD detector is coupled with an evaluation device of the state and/or intensity of its irradiation. CCD detectors are used as detectors of radiation, monitoring the yarn to be measured discontinuously always on very short sections of approximately 10 μm in length.

The U.S. Pat. No. 6,242,755 B1 discloses a method for the contactless measuring of fibrous textile material of indeterminate length, in which the textile material is placed within a radiation range of at least one source of radiation and its shadow is projected by the radiation on a receiving device comprising a row of sensor cells arranged next to one another, whereby the receiving device is composed of a CCD detector. The diameter of the fibrous textile material is determined on the basis of the number of fully shadowed sensor cells and from the partial shadowing of one or two neighbouring sensor cells, the value of the partial shadowing being determined proportionally according to the amount of the partial shadowing to the amount of the fully shadowed sensor cells.

Known yarn cleaners based on linear CCD or CMOS optical detectors work with digital values of the number of the shadowed optical elements. Even though the patents CZ 286 113 and U.S. Pat. No. 6,242,755 disclose methods for the evaluation of the yarn diameter including the influence of the partially irradiated optical elements, such detectors have not yet been realized for direct application on production machines, very probably also due to the difficulties and disadvantages which have been overcome by the present invention. The processing of the analog signals from the individual optical elements of the detector, if not accompanied by other measures, such as those preventing electromagnetic disturbances, is complicated and does not lead to the desired effect.

The patent U.S. Pat. No. 6,219,135 (EP 1015873 B1) describes a configuration of an optical detector, combining analog and digital optical elements with the purpose of obtaining not only the information about the yarn diameter from the number of the shadowed digital optical elements, but also the information about its surface structure from the partially shadowed optical elements. Supposedly, this device is intended only for laboratory apparatuses. However, if the device is to be used as a measuring device online directly during the production of yarn, it has a number of shortcomings. Another disadvantage is the fact that the alternating current component of a signal from analog optical elements, defining the surface structure of yarn, is modulated at a relatively great direct current component which worsens its processing by an A/D converter. Another drawback is the fact that the analog signal is carried to be processed outside the detector itself and is therefore exposed to the influences of electromagnetic disturbances which are induced into the analog conductor from other devices of the machine operating in the vicinity. Apparently, disturbance-free environment can be realized when the optical detector is used in a laboratory, but not in the case when it is used as part of production machines.

The disadvantages during the processing of an analog signal were eliminated by a device for the contactless measuring of the properties of moving yarn according to the patent CZ 299684, in which a linear optical detector is incorporated into one semiconductor application specific integrated circuit (ASIC) along with at least a part of electronic circuits for the processing and/or evaluation of a signal of the linear optical detector, whereby the electronic circuits for the processing and/or evaluation of a signal of the linear optical detector are integrated along with the linear optical sensor on a common semiconductor support and/or mounted in one common case.

The advantage of such an arrangement is especially the fact that the initial operations of the processing and/or evaluation of a signal of the detector take place in one integrated circuit, and so the output signal is not influenced by disturbances. Nevertheless, the solution according to CZ 299 684 is based only on the binary processing of the signals from the individual optical elements when only the irradiation or shadowing of each individual optical element is monitored. The drawback of this solution is a purely digital evaluation of the individual optical elements, when, according to a set comparison level, the individual optical elements are divided into irradiated and non-irradiated, the information about the yarn diameter is represented by the sum of the width of the shadowed optical elements. This device, therefore, does not permit a sufficiently precise evaluation of the surface structure of yarn and, moreover, it is immensely difficult to monitor a possible contamination of the individual optical elements with dust or other impurities or to monitor changes in the intensity of the light source.

SUMMARY OF THE INVENTION

An aim of the invention is to further increase the precision of monitoring the parameters of yarn in an electronic yarn cleaner by means of a linear optical detector, to obtain substantially more accurate information about the surface structure of yarn directly on a machine producing yarn, to prolong the time interval during which the linear optical detector is able to measure precisely without the operator intervention by improvement of monitoring of parameters of its sensor, and to create an option of warning the operator or an option of stopping an operating unit upon an occurrence of error in the function of the sensor of the optical detector. Another goal of the invention is using a sensor of an optical detector in optical detectors with different radiation sources, whereby the working point of the sensor is always optimally adjusted.

Additional objects and advantages of the invention will be set forth in part in the following description.

The aim of the invention is achieved by a method for monitoring at least one parameter of the quality of yarn and/or the parameters of the sensor in the electronic yarn cleaner according to the invention, whose principle consists in that in the first and/or in the second rows of optical elements of the sensor, there are for each monitored parameter of the quality of yarn and/or parameter of the sensor selected individual optical elements of the sensor constituting an active zone for monitoring the particular parameter. The number of the optical elements in one active zone in one row is lower than the overall number of the optical elements in the corresponding row, and the output analog signal of the individual optical elements of the corresponding active zone is included in the evaluation of the particular parameter.

The selection of the optical elements and their formatting into the active zones according to the monitored parameter allows the evaluation of several parameters of the quality of yarn or the parameters of the sensor during one measurement cycle. Dividing the optical elements into the active zones aimed at a particular monitored parameter results in increasing measurement accuracy, achieving more precise classification of yarn defects, improving measurement dynamics, suppressing the influence of the optical elements which are not needed for the monitored parameter, and suppressing the influence of the contamination of the detector with dust, as well as suppressing the influence of ambient light.

Especially for monitoring the diameter of yarn and yarn diameter defects or some parameters of the sensor, it is advantageous if the active zone is formed by a continuous row of optical elements.

For monitoring other parameters of the quality of yarn or the parameters of the sensor, it is advantageous if the active zone is formed by two or more groups of optical elements which are separated from one another and situated in at least one row of optical elements.

In order to improve the measurement dynamics, it is advantageous if the size and position of at least one active zone for monitoring the parameter of the quality of yarn during the operation of the optical detector changes depending on the current position of the projection of yarn images, preferably for example according to CZ 299684.

An active zone for monitoring the parameters of the quality of yarn is formed in the area of the projection of yarn images on the optical elements of the first row and/or the optical elements of the second row and in the vicinity of this projection of yarn. Thus, the dynamics of the output signal improves and, at the same time, the influence of the optical elements which are not included in the active zone is limited. However, if the active zone was not formed and all the optical elements were evaluated, they could influence the monitored parameter, for example in case these optical elements become contaminated.

Furthermore, an active zone for monitoring the yarn diameter and yarn diameter defects is formed by a continuous row of optical elements. The continuous row of optical elements corresponds to the size of the projection of yarn enlarged by the assumed size of yarn defects.

In addition, an active zone for monitoring the surface structure of yarn is formed by two groups of optical elements of the first row separated from one another, and/or by two groups of optical elements of the second row separated from one another, or by a continuous row of optical elements of the second row, whereby at least all the partially shadowed optical elements of the second row are part of this active zone.

It is always advantageous to monitor a particular parameter of the quality of yarn on the smallest possible amount of optical elements which are influenced by a change of this parameter, and as a result of a change of the monitored parameter their output analog signal changes. Therefore, for example for monitoring the surface structure of yarn, two active zones are formed in the first row on the edges of the projection of yarn. For sufficiently coarse types of yarn, whose diameter exceeds the width of at least two optical elements of the second row, the same division can be applied also in the second row of optical elements. For very fine yarns in the second row it is more advantageous to form an active zone for monitoring the surface structure of yarn by a continuous row of optical elements.

For monitoring the parameters of the sensor, it is advantageous if the active zone for this monitoring is formed outside the area of the projection of yarn images on the optical elements of the first and/or second rows. On the optical elements outside the area of the projection of yarn images, the output signal should be substantially constant, independent of the measured yarn, and, consequently, it is possible to easily monitor a possible change caused by external influences, such as the aging of the light source or contamination with dust. Simultaneously, at least two active zones can be formed in one row or in both rows of optical elements, whereby at least some optical elements can be part of more active zones.

In case of a change of the type of spun-out yarn the active zone/zones changes/change in size and/or selection of individual optical elements according to the width of the projection of yarn images.

DESCRIPTION OF DRAWINGS

An example of embodiment of a detector, on which the method according to the invention can be applied, is schematically shown in the enclosed drawings, where:

FIGS. 3 and 4 show examples of selection of optical elements of the sensor of the optical detector for the active zones.

DETAILED DESCRIPTION OF PARTICULAR EMBODIMENTS

Figure 1:
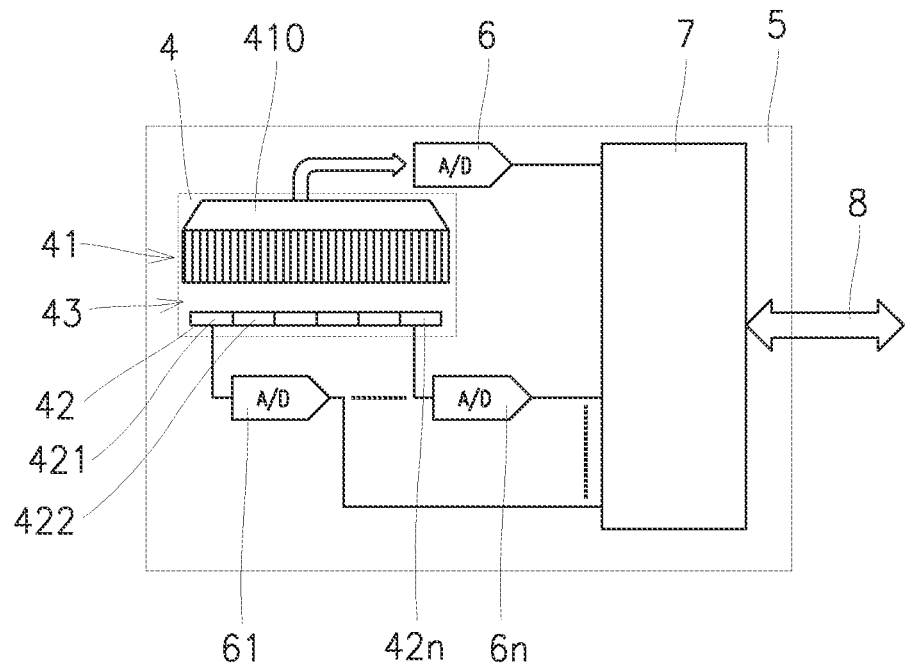
FIG. 1 shows an arrangement of the optical detector with the sensor.

Reference will now be made to embodiments of the invention, one or more examples of which are shown in the drawings. Each embodiment is provided by way of explanation of the invention.

The method for monitoring at least one parameter of the quality of yarn by an electronic yarn cleaner will be explained on an example of embodiment of an electronic yarn cleaner comprising an optical detector for monitoring the parameters of moving yarn on textile machines, for example, on the spinning machines or weft-winding machines.

The cleaner 1 of yarn comprises a case 11, in which a groove 111 is formed for the passage of yarn 2. The groove 111 is open on one side, which enables to insert the yarn 2 into the groove 111. Arranged opposite each other in the side walls of the groove 111 are an output portion of a source 3 of radiation and a sensor 4 of an optical detector 5.

In the illustrated embodiment the source 3 of radiation comprises a light-emitting diode (LED) 31 and an optical lens 32 serving to create a bundle of parallel rays passing through the groove 111 and projecting a shadow on the sensor 4 of the optical detector 5, as a result of the perpendicular projection of yarn 2. The light-emitting diode LED 31 of the source 3 of radiation is aligned with a control circuit 33 of radiation intensity, which is connected to a programmable device 9 of the cleaner 1 of yarn 2, from which it receives, if necessary, commands to change the intensity of radiation. The programmable device 9 is by a communication data bus 10 connected to other members of an operating unit of a machine.

The sensor 4 of the optical detector 5 comprises in the illustrated embodiment two parallel rows of optical elements. The optical elements 41 of the first row are rectangular-shaped and are oriented to have their longer sides in a direction along the movement of the projection of yarn 2. The optical elements 42 of the second row are also rectangular-shaped, but they are oriented to have their longer sides perpendicular to the direction of the movement of the projection of yarn 2. At the output of the optical elements 41 of the first row, as well as at the output of the optical elements 42 of the second row, there is an analog signal proportional to the intensity of irradiation or shadowing of the optical elements 41, 42. The optical elements 41, 42 of both rows are made by CMOS technology. FIGS. 3 and 4 show schematically the optical elements 41, 42 of the sensor 4, on which the yarn 2 is projected, whereby black colour in the individual optical elements 41, 42 indicates the size of the analog signal produced by the irradiated or partially irradiated optical elements 41, 42. To simplify the drawings, the gap spaces between the individual optical elements 41, 42 have been omitted.

In an unillustrated embodiment, the sensor 4 comprises only one row of optical elements corresponding by their size and orientation either to the optical elements 41 of the first row, or to the optical elements 42 of the second row.

Figure 2:
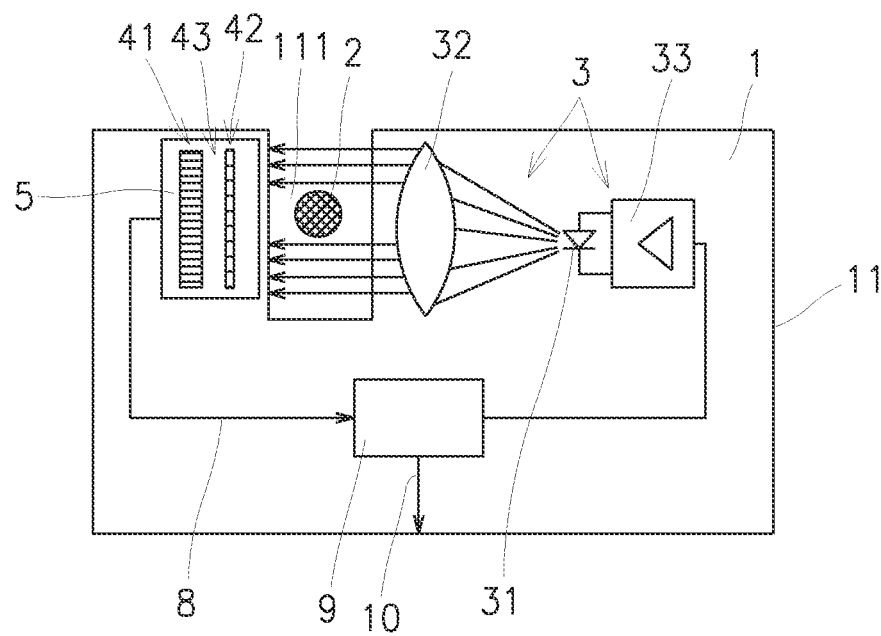
FIG. 2 illustrates an arrangement of a yarn cleaner with the optical detector.

The optical detector 5 comprises a sensor 4 with two rows of optical elements 41, 42, between which there is a distance 43. The outputs of the optical elements 41, 42 are processed in an analog manner and subsequently by the analog-to-digital converters in order to obtain the precise value of the intensity of irradiation of the optical elements 41, 42 of each row. The sensor 4, or, in other words, both rows of its optical elements 41, 42 are schematically represented in FIG. 2 so as to explain the invention with the aim of helping to a better understanding of the characteristics of the invention. In a practical embodiment, they are arranged in the groove 111 opposite the source 3 of radiation.

An example of a connection of the optical detector 5 is schematically represented in FIG. 1, where the dashed line indicates a semiconductor support of the optical detector arranged on which is a sensor 4 and on it the first row of optical elements 41 and the second row of optical elements 42. The outputs of the individual optical elements of the first row are through one or several analog multiplexers 410 connected to one or several analog-to-digital converters 6, whereby in the illustrated embodiment there are used one multiplexer 410 and one analog-to-digital converter 6. The second row is parallel with the first row and the output of each individual optical element 421, . . . 42$n$ of the second row is connected to the inlet of the analog-to-digital converter 61, . . . 6$n$. The outputs of all the analog-to-digital converters 6, 61, . . . 6$n$ are interconnected with the inlet of the programmable device 7 of the optical detector 5.

The analog signal at the output of the individual optical elements 41, 42 is monitored in cycles and evaluated. During each measurement cycle for the monitored parameter of the quality of yarn 2 and/or for the monitored parameter of the sensor 4 individual optical elements 41, 42 of the sensor 4 are selected and their output signal will be included in the evaluation of the particular parameter. In this manner, for each monitored parameter an active zone, optimized for monitoring it, is formed. The active zones can be formed in the first row of optical elements 41 or in the second row of optical elements 42 or in both rows of optical elements 41, 42. Furthermore, it is advantageous to monitor each parameter of the quality of yarn on the smallest possible amount of the optical elements which are influenced by a change of this parameter, their output signal being changed as a result of the change of this parameter. On the other hand, for monitoring the parameters of the sensor, it is advantageous to monitor a particular parameter on the largest possible amount of the optical elements, uninfluenced by the projection of yarn 2 images.

The basic monitored parameters of yarn 2 are the diameter and diameter defects of yarn 2 and the surface structure of yarn 2, such as hairiness.

The basic monitored parameters of the sensor 4 are the contamination of the optical elements 41, 42 of the sensor 4 with dust and the influence of ambient light and/or the aging of the source 3 of light.

An active zone for monitoring the selected parameter of the quality of yarn 2 is formed in the area of the projection of yarn 2 images on the optical elements 41, 42 of the sensor 4 and in the vicinity of this projection of yarn 2. What is meant by the expression "in the vicinity" is in the first row of optical elements 41 several optical elements on each side of the projection of yarn 2, whose number corresponds at least to the assumed size of the defects of yarn 2, and in the second row of optical elements 42 usually the last partially shadowed optical element 42 on each side of the projection of yarn 2. Also in the second row of optical elements 42 "the vicinity" can include at least one optical element 42 of the sensor 4 non-shadowed by the projection of yarn 2 on each side of the projection of yarn 2.

For monitoring the diameter of yarn 2 and monitoring diameter defects of yarn 2 an active zone Z1.1, Z2.1 is formed by a continuous row of optical elements 41, 42 of the first and/or of the second rows, whereby the continuous row of the optical elements 41, 42 is situated in the area of the projection of yarn 2 and in its vicinity and the number of the optical elements 41, 42 in one row is smaller than is the overall number of the optical elements 41, 42 in the corresponding row.

For monitoring the surface structure of yarn 2 two groups of optical elements 41 of the first row, separated from one another, form on the edges of the projection of yarn 2 images active zones Z1.2.1, Z1.2.2 and/or two groups of optical elements 42 of the second row separated from one another, on the edges of the projection of yarn 2 form active zones Z2.2.1, Z2.2.2 or a continuous row of optical elements 42 of the second row across the whole projection of yarn 2 images form an active zone Z2.2.3, which is advantageous for very fine yarns 2, whose projection is smaller than the width of two optical elements 42 of the second row.

For monitoring the parameters of the sensor 4 active zones are formed outside the area of the projection of yarn 2 images on the optical elements 41, 42 of the first and/or second rows, since the analog output signal on these optical elements 41, 42 is substantially constant and therefore it is easy to monitor its possible change.

For monitoring the contamination of the sensor 4 of the optical detector 5 with dust, an active zone Z1.3 is formed outside the area of the projection of yarn 2 in the first row of optical elements 41 and/or an active zone Z2.3 is formed in the second row of optical elements 42, whereby typically, these zones are situated one above the other.

So as to monitor the influence of ambient light and/or the aging of the source 3 of light, an active zone Z1.4 is formed outside the area of the projection of yarn 2 on the optical elements 41 of the first row and/or an active zone Z2.4 is formed outside the area of the projection of yarn 2 on the optical elements 42 of the second row, whereby these zones are typically situated one above the other.

The size and position of the individual active zones change during the operation of the optical detector 5 dependent on the position of the projection of yarn 2, whereby the position of the projection of yarn 2 is determined for example according to the patent CZ 299684.

On the sensor 4 in individual rows of optical elements 41, 42, two or more active zones can be formed, whereby at least some optical elements 41, 42 can be part of several active zones.

With a change of the type of spun-out yarn 2 on the machine, the active zone/zones changes/change in size and/or and/or selection of the individual optical elements 41, 42 according to the width of the projection of yarn 2 images on the individual optical elements 41, 42.

LIST OF REFERENCES

1 yarn cleaner
11 case of the yarn cleaner
111 groove
2 yarn
3 radiation source
31 light-emitting diode LED
32 optical lens
33 control circuit of the intensity of radiation
4 sensor of the optical detector
41 optical elements of the first row
410 analog multiplexer
42 optical elements of the second row
421, . . . 42n individual, optical elements of the second row
43 distance between the first and the second rows of optical elements
5 optical detector
6, 61, . . . 6n analog-to-digital converters
7 programmable device of the optical detector
8 communication data bus of the optical detector
9 programmable device of the yarn cleaner
10 communication data bus of the yarn cleaner
Z1.1 active zone in the first row for monitoring, the diameter of yarn and yarn diameter defects
Z2.1 active zone in the second row for monitoring the diameter of yarn and yarn diameter defects
Z1.2.1 active zone in the first row for monitoring the surface structure of yarn
Z1.2.2 active zone in the first row for monitoring the surface structure of yarn
Z2.2.1 active zone in the second row for monitoring the surface structure of yarn
Z2.2.2 active zone in the second row for monitoring the surface structure of yarn
Z2.2.3 active zone continuous in the second row for monitoring the surface structure of yarn
Z1.3 active zone in the first row for monitoring the contamination of the sensor with dust
Z2.3 active zone in the second row for monitoring the contamination of the sensor with dust
Z1.4 active zone in the first row for monitoring the influence of ambient light and/or the aging of the light source
Z2.4 active zone in the second row for monitoring the influence of ambient light and/or light source

The invention claimed is:

1. A method for monitoring a yarn quality parameter or a sensor parameter in an electronic yarn cleaner having an optical detector with a sensor having one or two rows of individual optical elements having a rectangular shape and that produce an analog output signal proportional to irradiation intensity on the respective optical element, wherein a value of intensity of the irradiation is monitored during a measurement cycle, the method comprising:

for each particular yarn quality parameter or sensor parameter that is monitored in each measurement cycle, selecting an active zone of the optical elements within at least one of the rows of optical elements whose output analog signals are evaluated for the particular yarn quality parameter and sensor parameter;

evaluating the particular yarn quality parameter or sensor parameter as a function of the output analog signals from the optical elements within the active zone;

wherein for each monitored yarn quality parameter, a lowest possible number of the optical elements in the active zone are monitored whose respective output analog signal changes due to a change in the yarn quality parameter; and wherein for each monitored sensor parameter, a highest possible number of the optical elements in the active zone whose respective output analog signal is not affected by a yarn image projection are monitored.

2. The method as in claim 1, wherein the active zone is designated as a continuous subset of optical elements within the respective row of optical elements.

3. The method as in claim 1, wherein the active zone is designated as multiple spaced apart groups of optical elements within the respective row of optical elements.

4. The method as in claim 1, further comprising varying a size and position of the active zone within the respective row of optical elements during operation of the optical detector as a function of changes in position of a yarn image projection on the sensor.

5. The method as in claim 1, wherein the active zone is designated for monitoring a yarn quality parameter and includes optical elements within the respective row of optical elements corresponding to a yarn image projection area on the sensor and a designated number of vicinity optical elements beyond the yarn image projection.

6. The method as in claim 5, wherein the monitored yarn quality parameter is yarn diameter or diameter defects, and wherein the active zone is designated as a continuous group of optical elements within the respective row of optical elements.

7. The method as in claim 5, wherein the monitored yarn quality parameter is surface structure of the yarn, and the active zone is designated as one or a combination of: two groups of spaced apart optical elements within a first row of optical elements; two groups of spaced apart optical elements within a second row of optical elements that is behind the first row of optical elements; or a continuous subset of optical elements within the second row of optical elements, and wherein all of partially shadowed optical elements within the second row are included in the active zone.

8. The method as in claim 1, wherein the active zone is designated for monitoring a sensor parameter and includes optical elements within the respective row of optical elements that are outside of a yarn image projection area on the sensor.

9. The method as in claim 8, wherein the sensor parameter is dust or other contamination on the optical elements.

10. The method as in claim 8, wherein the sensor parameter is one of ambient light on the optical elements, or decreasing intensity of irradiation on the optical elements due to aging of a radiation source.

11. The method as in claim 1, wherein multiple active zones are designated for monitoring one or more yarn quality parameters, and wherein individual optical elements within the respective row of optical elements belong to two or more of the active zones.

12. The method as in claim 1, wherein one or more active zones are designated for monitoring one or more yarn quality parameters, and wherein the size and designation of optical elements within the active zone are changed as a function of changes in a type of yarn being monitored, wherein different monitored yarns have different widths of a yarn image projection on the sensor.

* * * * *